United States Patent [19]
Fraser

[11] Patent Number: 5,965,850
[45] Date of Patent: Oct. 12, 1999

[54] NON-ELECTRONIC HEARING AID

[75] Inventor: Robert D. Fraser, Windosr, Calif.

[73] Assignee: Fraser Sound Scoop, Inc., San Francisco, Calif.

[21] Appl. No.: 08/890,909

[22] Filed: Jul. 10, 1997

[51] Int. Cl.[6] .................................................. H04R 25/00
[52] U.S. Cl. ........................... 181/129; 181/133; 181/136
[58] Field of Search ..................... 181/129, 133, 181/136; 2/209; 381/183, 187

[56] References Cited

U.S. PATENT DOCUMENTS

| | | |
|---|---|---|
| 20,871 | 10/1858 | Donoher . |
| 292,916 | 11/1884 | Ikeda . |
| 656,182 | 8/1900 | Ehrhardt . |
| 1,453,969 | 5/1923 | Brown . |
| 1,708,257 | 4/1929 | Campbell . |
| 2,537,201 | 1/1951 | Amfitheatrof . |
| 3,938,616 | 2/1976 | Brownfield . |
| 4,556,122 | 12/1985 | Goode . |
| 4,574,912 | 3/1986 | Fuss et al. . |
| 4,771,859 | 9/1988 | Breland . |
| 4,890,688 | 1/1990 | Baker . |
| 4,997,056 | 3/1991 | Riley . |
| 5,661,270 | 8/1997 | Bozorgi-Ram ........................... 181/129 |

*Primary Examiner*—Khanh Dang
*Attorney, Agent, or Firm*—Flehr Hohbach Test Albritton & Herbert LLP

[57] ABSTRACT

An acoustic hearing aid comprising: (a) a pair of thick-walled, sound collector cups (12) each shaped to fit over the pinna (20) of a user's ear, turning the back of pinna (21) forward, and each constructed of a sound reflective material of sufficient thickness to provide insulation against sound transmission therethrough from a side (19) of collector cups (12), collector cups (12) each having a C-shaped ridge (17) of substantial thickness dimension formed for engagement of the user's head immediately proximate and around the user's pinna (20), ridge (17) extending from a position in front of the top of pinna (20) and above the level of ear canal (22) around pinna (20) to a position below earlobe (23), collector cups (12) each further extending outwardly from ridge (17) and away from the user's head and extending forwardly in a generally parallel relation to the user's head to a position in advance of ear canal (22) to reduce sound transmission to the user's ears from the sides of the user's head, collector cups (12) each terminating in a forwardly facing, substantially vertically oriented, generally rectangular opening (25) for receipt and collection of sound emanating from the front of the user; and (b) an arcuate headband (14) constructed of a resiliently flexible material and having collector cups (12) mounted proximate opposite ends thereof, headband (14) being dimensioned to apply a resilient biasing force to collector cups (12) to bias C-shaped ridge (17) into contact with the user's head proximate the user's ears to transmit collected sound vibrations through C-shaped ridge (17) to the user's bone structure proximate the ears and resist the entry of sounds other than from in front of the user from entering said collector cups.

8 Claims, 6 Drawing Sheets

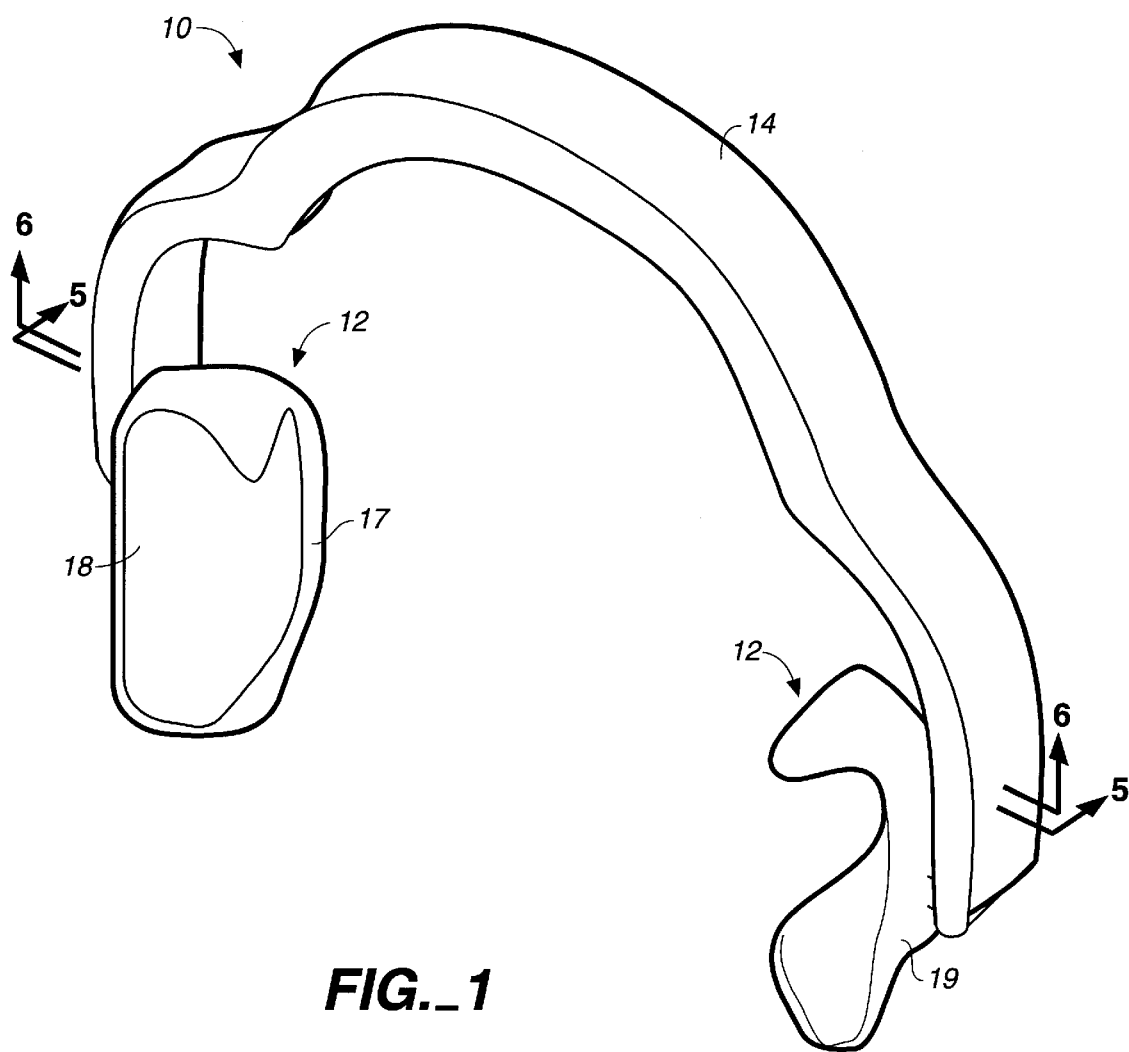
FIG._1

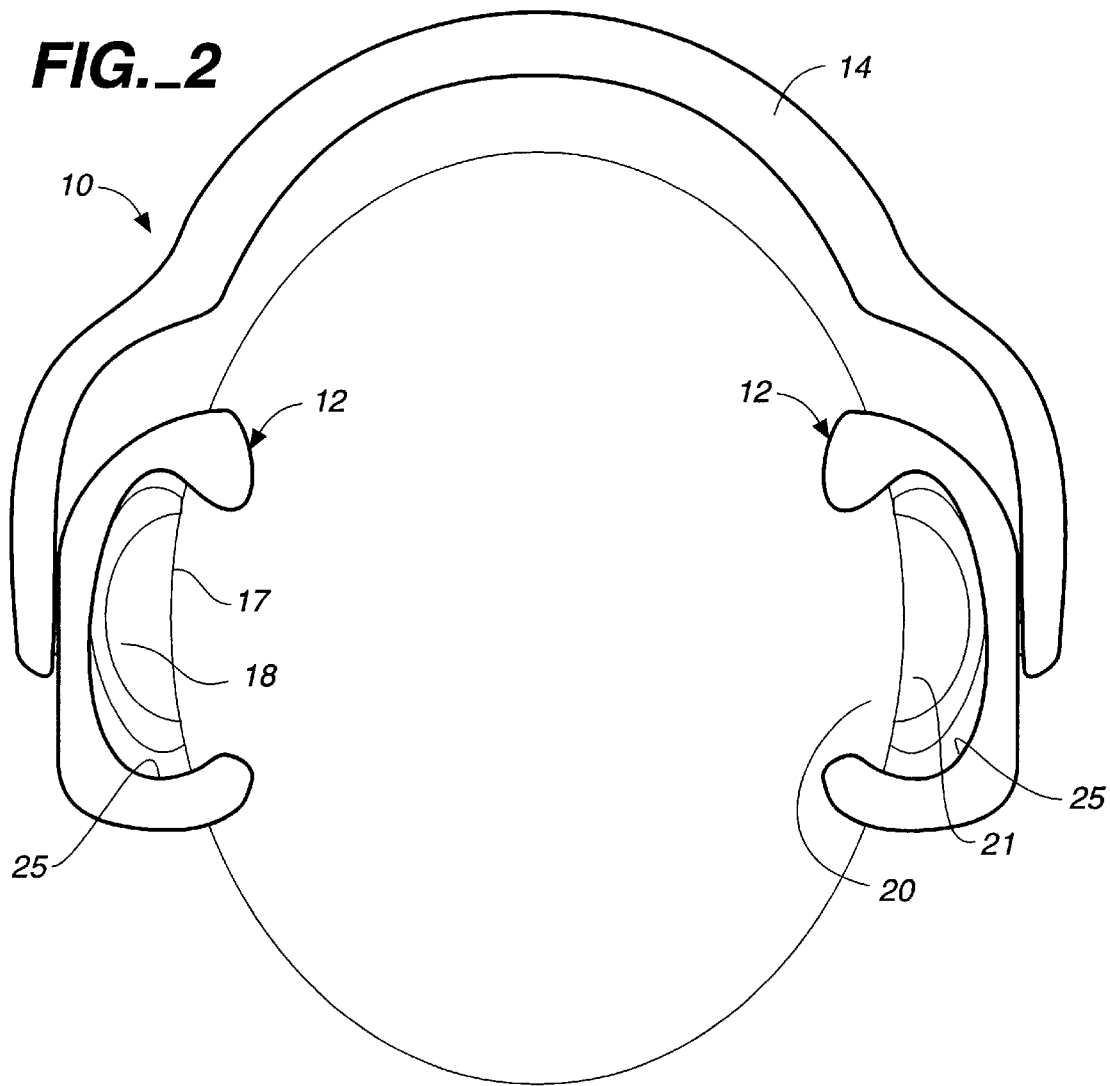
FIG._2

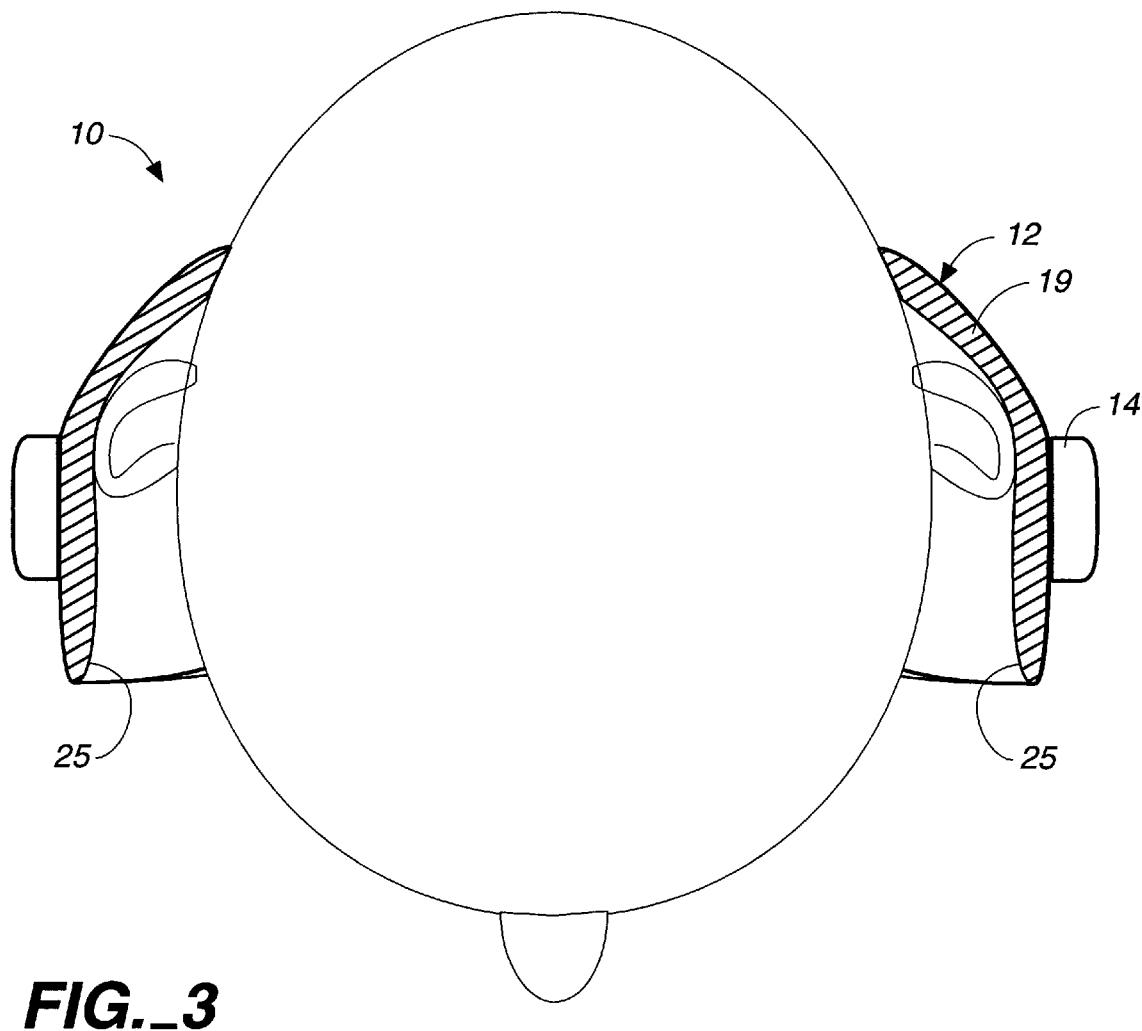
FIG._3

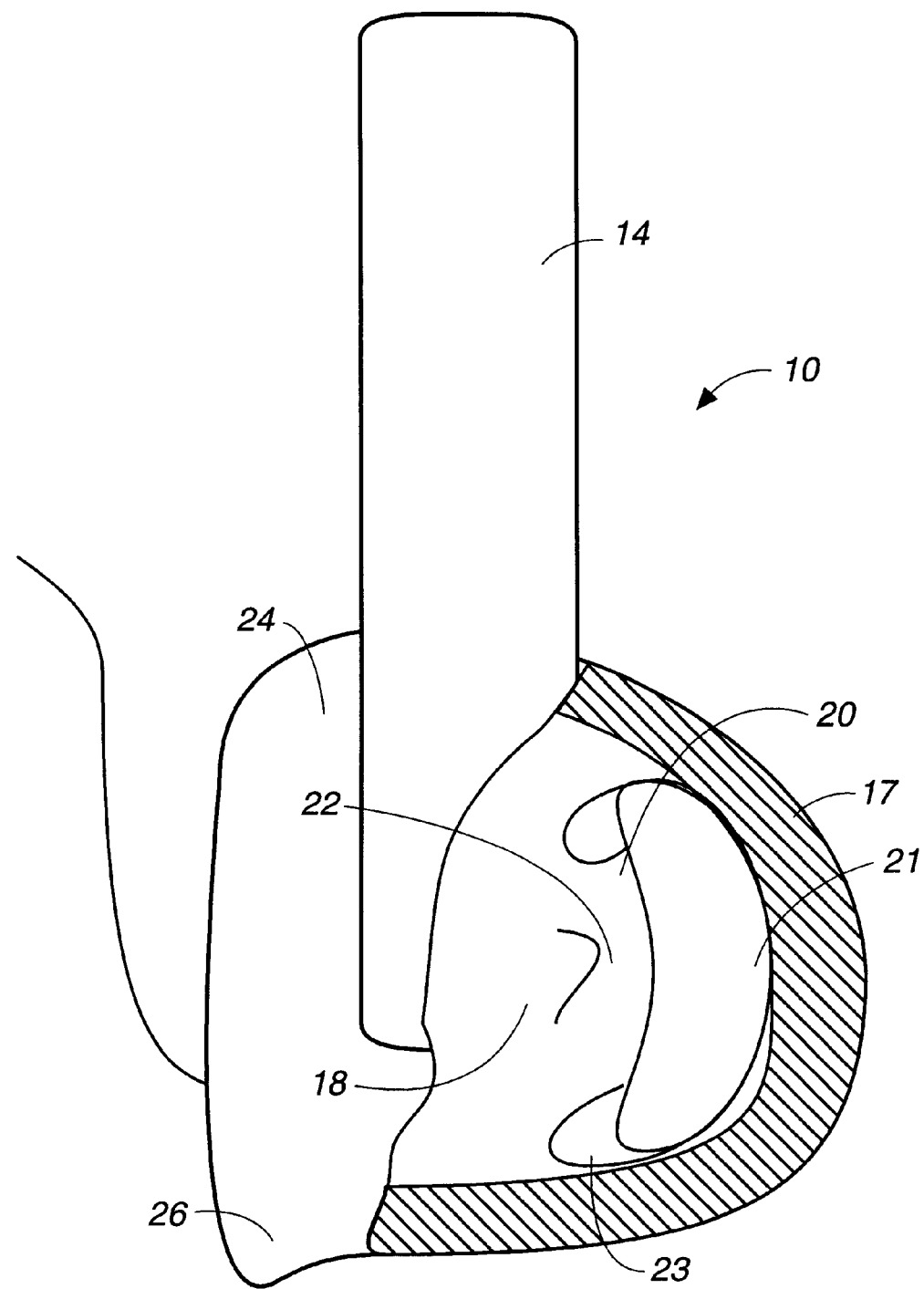
FIG._4

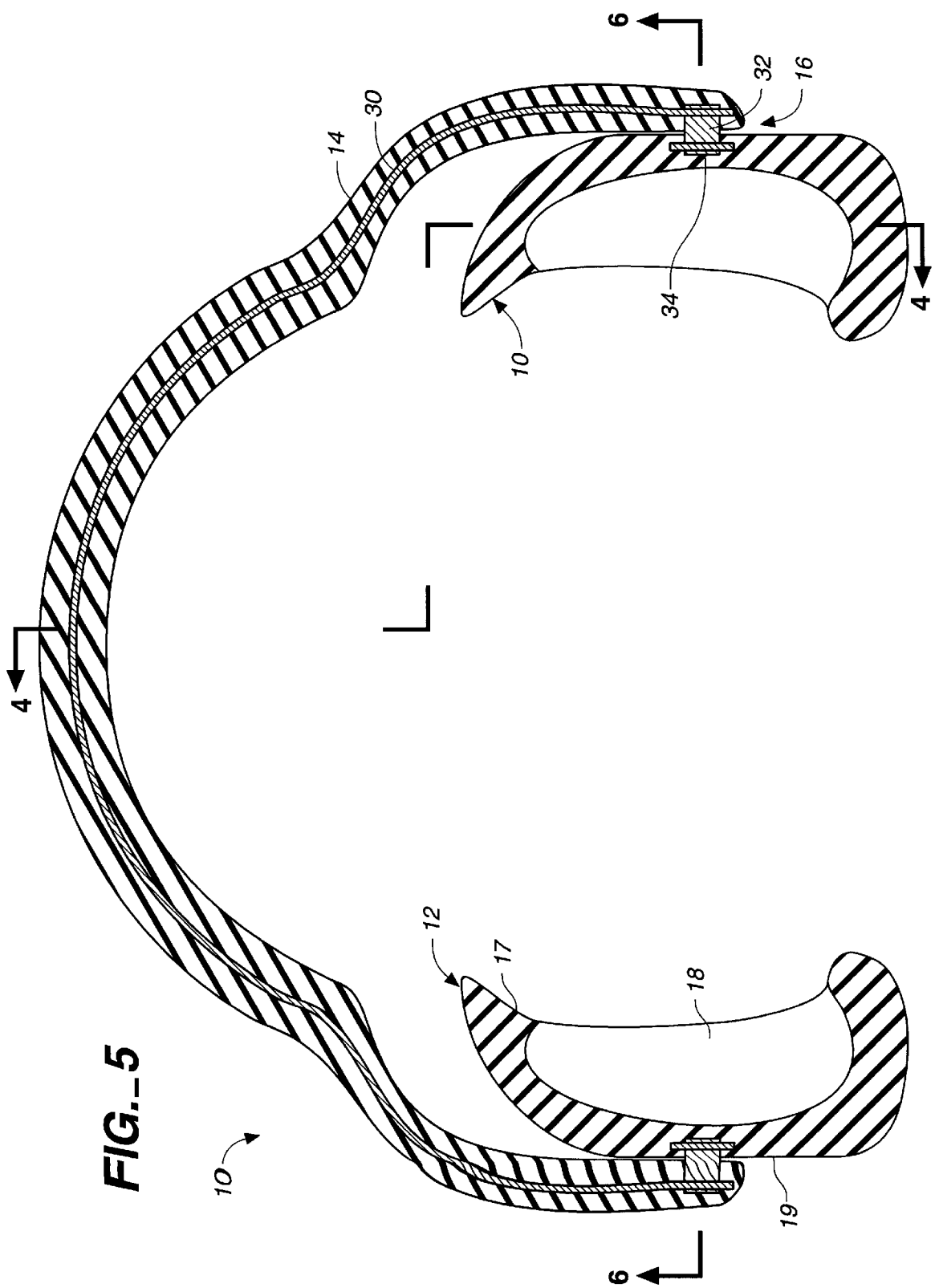

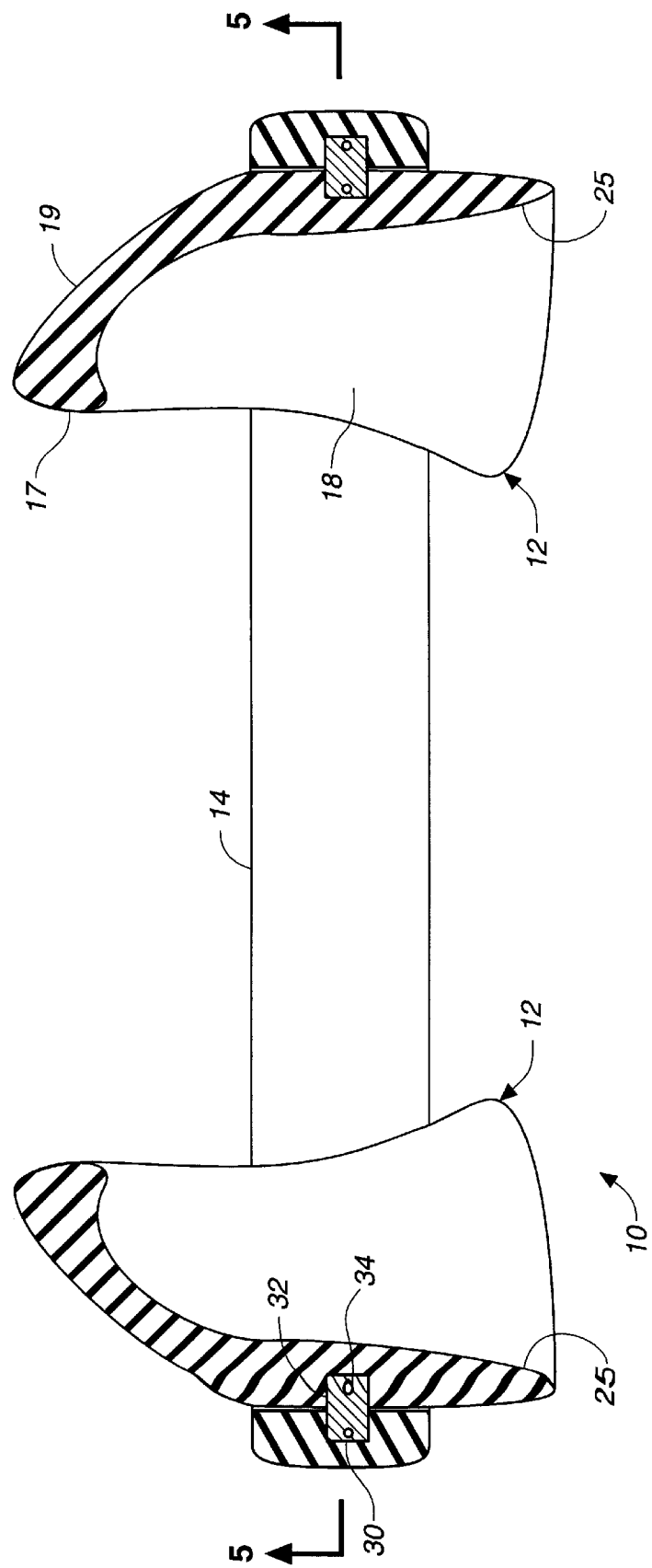
FIG._6

NON-ELECTRONIC HEARING AID

TECHNICAL FIELD

The present invention relates to hearing aids, and more particularly to acoustic or non-electronic hearing aids.

BACKGROUND

1. Non-Electronic Hearing Aids

Non-electronic hearing aids have been around for many years and their development has traditionally preceded electronic hearing aids. Unfortunately, the cost of purchasing and repairing today's electronic hearing aids has become quite substantial. In fact, today's electronic hearing aids may easily cost upwards of $2000 each. For a typical user, this cost is frequently doubled as users often wear hearing aids in both ears. The cost of these expensive electronic hearing aids is often not covered by medical insurance or Medicare. In addition, electronic hearing aids require a continual supply of new batteries. As a result, a need exists for an effective inexpensive acoustic or non-electronic hearing aid manufactured without the need for any internal expensive electrical componentry.

Many different forms of acoustic hearing aids have been developed, both pre-dating and concurrent with the development of electronic hearing aids. All of these non-electronic hearing aids can, however, typically be conveniently analyzed as belonging to one or the other of the following two separate families of hearing aids.

A first family of non-electronic hearing aids consists of a large outwardly-protruding cup or scoop for capturing and focusing sound waves into a user's ear canal. An early development of such a device is found in U.S. Pat. No. 656,182 to Ehrhardt. This device consists of two hollow truncated cones or scoops which each fit around the user's ears. The novel aspect of this invention was that it could be conveniently attached to the user's head by use of a head band, so as to avoid the necessity of being held by the hand, as was the case for pre-existing ear trumpets.

U.S. Pat. No. 1,708,257 to Campbell also disclosed a sound wave catcher which physically contacts the back of the user's ear and conducts sound waves into the user's ears. As such, the operation of this device resembles the use of the hand being cupped behind and outside of the ear. A novel aspect of this invention was that the sound wave catcher could be folded so as to be carried in a vest pocket or other small space.

U.S. Pat. No. 2,537,201 to Amfitheatrof disclosed a pair of cupped-shaped sound collectors which fit behind the user's ears and are connected together by a head band passing over the user's head. The novel aspect of this invention was that the sound cups or baffles could be selectively regulated by extending them such that the surface area of the overall sound gathering cup could be varied.

U.S. Pat. No. 3,938,616 to Brownfield disclosed a sound multiplier comprised of a pair of thin cups mounted on a person's head which are held in position by a head band such that these cups fits sealingly about a person's ear. The cups are separated from the sides of the wearer's head by a layer of felt. These cups have a spiral contour opening which is approximately co-incident with the front face of the user.

U.S. Pat. No. 4,574,912 to Fuss, et al. disclosed an earmuff hearing aid consisting of a pair of thin-shelled outwardly-extending ear extenders transversely in contact with the listener's head behind the user's ears. These extenders were held in position by a head band. Having these extenders positioned behind the ears and in contact with the listener's head, sounds were thereby amplified and transmitted directly into the user's ears.

U.S. Design Pat. No. 292,916 to Ikeda shows an ornamental design for a scoop-type non-electronic sound amplifier.

U.S. Pat. No. 4,771,859 to Breland disclosed a hearing aid apparatus consisting of two cupped-shaped members with sound reflective surfaces which direct sound waves into the user's ears. Also disclosed in this design is the modified embodiment of the invention using a foam padding in a rear portion of the cupped-shaped members to cause a gentle forward bending of the user's ears to further increase hearing ability.

U.S. Pat. No. 4,997,056 to Riley discloses an ear-focused acoustic reflector. This device mechanically intercepts frontally-generated sound waves in a manner that accurately preserves their phase coherency at all frequencies, and then reflects these sounds into the ear canals of the listener. To accomplish this, the Riley device uses a pair of acoustic reflectors which are parabolically shaped and are held in position by a head band passing over the user's head. The Riley device further uses acoustically damping material which operates to prevent the amplifying of sound vibrations emanating from sources not directly in front of the user. Accordingly, the Riley device allows the user to actively select the sound source to be amplified, while blocking out unwanted sounds. Specifically, sounds coming from other sources are not amplified as an acoustic dampening pad is provided on the reflectors such that any unwanted vibrations intercepting the reflectors are not transmitted by bone conduction into the ears. Accordingly, the object of the Riley device is to increase the degree of acoustic fidelity which a listener hears emanating from an audio system's loud speaker by providing a very directionally selective system which operates to shield the listener from sounds emitted from other sources.

The disadvantages of this first family of hearing aids are numerous. First, they all are rather large in size. Using large outwardly-scooped cup or parabolic-shaped sound reflectors, this family of hearing aids consumes considerable space. Secondly, these devices tend to be quite wide, spanning a large distance between their lateral ends and the user's ears. These two disadvantages combine to produce a third disadvantage, namely that the device is not aesthetically appealing to a typical user.

A second family of acoustical hearing aid devices operate on the principle of inserting a thin tubular-shaped member directly into the user's ear canal while concurrently covering this region with a second external member having a small opening such that this external member encloses a small cavity of air while covering the first internal member.

A first example is found in U.S. Pat. No. Re. 20,871 to Donoher which discloses a simple auricle having a wig hair covering placed thereover.

U.S. Pat. No. 1,453,969 to Brown discloses a second example of an auricle device. This device operates to intensify sound wave vibration reflected into the ear canal and the external member of this device engages the side of the head to transmit vibrations into the bones of the skull.

U.S. Pat. No. 4,556,122 to Goode discloses a similar device. This device modifies the normal concha resonance and combines it with the ear canal resonance to shift the normal sound pressure gain of 15 to 20 decibels at the tympanic membrane downward from 2,600 to 3,000 kilohertz to 1,500 to 2,000 kilohertz. A 5–15 dB increase in sound pressure is generated in the 1000–2500 Hz range. To achieve this, the Goode device provides a thin hollow shell that fits snugly into the auricle and concha of the external ear so as to enclose a volume of air within the concha. An opening in the shell lets sound waves into this air volume. The proper ratio of this air volume to the area of the opening in the shell controls the peak frequency of amplification desired, the amplitude and also the bandwidth of amplification. Accordingly, the Goode device is able to provide significant sound amplification for persons with mild high frequency hearing loss. By varying the volume of this chamber and the area of the opening within a certain range, the resonance frequency of the device can be adjusted to meet the specific hearing amplification needs of a particular individual suffering from mild hearing loss.

A first disadvantage with this second family of hearing aids is that they are limited over the range of frequencies with which they selectively operate. Furthermore, using a device such as the Goode device, the desired frequencies over which this device is to operate must be pre-set for each particular user. This pre-setting is done by modifying the structure of the device itself. Once this modification has been made, the device can not be re-modified for another range of frequencies. This second family of hearing aids is also limited by the fact that it employs an invasive internal member which is typically tubular in shape and fits into the user's ear canal. A less intrusive device, avoiding this feature, would instead be much more desirable. Operating on the principle of selectively vibrating at certain resonance frequencies, this second family of devices does not truly catch, funnel or reflect a broad spectrum of sound waves, concentrating these sound waves in the user's ears as was accomplished by the first family of hearing aids. Therefore, a third disadvantage of this second family of hearing aids is that sound vibrations are transmitted directly into the ear canal regardless of the direction from which the sounds are emanating. Accordingly, any directional selectivity enabling the user to choose to listen to one particular sound source is reduced, impaired or non-existent in the second family of non-electronic hearing aids. This presents problems for some hearing-impaired persons who have trouble distinguishing between various sound sources.

Lastly, an anechoic ear piece which can not be easily classified into either of the above two families of devices exists as found in U.S. Pat. No. 4,890,688 to Baker. This anechoic ear piece does not operate to amplify sounds and is therefore only marginally related to the present invention. Instead, this device is simply designed to block out the reception of all sound waves approaching the ears with the sole exception of sound waves emanating from a source directly in front of the listener, preferably being the sound waves coming from a stereo speaker.

In light of the existing prior art and its associated limitations, a long-felt need exists for a hearing aid device which would combine the positive features of the first and second families of non-electronic hearing aids while overcoming the limitations of both these families. Specifically, a need exists for a device which is able to gather and reflect into the ear more sound waves than would otherwise normally be received by the ear in the absence of such a device. These sound waves should be collected and directed into the ear canals using a device which does not require the large, wide sound reflectors as seen in the first family of prior art hearing aids. In addition, this new device should operate well over a wide range of frequencies, be directionally selective, not require non-reversible structural modifications or adjustments be made for each user, and not require invasive tubular members be inserted into the inner ear, thus overcoming the problems inherent in the above second family of non-electronic hearing aids. Accordingly, the preferred device should not entail sound collectors extending too far beyond the sides of the ear and should be able to effectively gather and reflect sound waves into the ear canal over a wide variety of frequencies. This device should also have the added advantage of transmitting sound waves directly into the ears through conduction in the skull bones of the user. Furthermore, this device should be directionally selective such that the user may, simply by orienting his or her head towards a particular source of emitted sound waves, amplify particular sounds as desired.

2. Objects of the Invention

It is an object of the present invention to provide an acoustical hearing aid device which employs no electrical or electronic circuit components.

It is a further object of the present invention to provide a versatile acoustic hearing aid which is very inexpensive.

It is a further object of the present invention to provide an acoustical hearing aid which does not have a cosmetically or aesthetically objectionable large size or laterally extending width. This device should also be lightweight.

It is a further object of the present invention to provide an acoustical hearing aid which gathers and reflects sound waves into a user's ear canals over a wide range of frequencies.

It is a further object of the present invention to provide a non-electronic hearing aid which does not require a tubular member be inserted into the user's ear canal.

It is a further object of the present invention to provide an acoustic hearing aid offering a gain in volume of approximately 25 decibels in the 1,500 kilohertz range.

It is a further object of the present invention to provide an acoustical hearing aid which is directionally selective such that the user can choose to amplify the sound waves emitted from a particular source or direction simply by reorienting his or her head.

It is a further object of the present invention to provide an acoustic hearing aid which does not require any permanent structural modifications to be made for each individual user.

It is a further object of the present invention to provide an acoustic hearing aid which is durable, reliable and easy to fabricate and which has no repair costs.

It is a further object of the present invention to provide an acoustical hearing aid which is lightweight, comfortable and easy to use.

DISCLOSURE OF THE INVENTION

The present invention discloses an acoustic hearing aid comprising (a) a pair of thick-walled, sound collector cups each shaped to fit over the pinna of a user's ear, turning the back of the pinna forward, each constructed of a sound reflective material of sufficient thickness to provide insulation against sound transmission therethrough from a side of the collector cups, the collector cups each having a C-shaped ridge of substantial thickness dimension formed for engagement of the user's head immediately proximate and generally around the user's pinna, the ridge extending from a position in front of the top of the pinna and above the level of the ear canal around the pinna to a position below the earlobe, the collector cups each further extending outwardly from the ridge and away from the user's head and extending forwardly in a generally parallel relation to the user's head to a position in advance of the ear canal to reduce sound transmission to the user's ears from the sides of the user's head, the collector cups each terminating in a forwardly facing, substantially vertically oriented, generally rectangular opening for receipt and collection of sound emanating from the front of the user; and (b) an arcuate headband constructed of a resiliently flexible material and having the collector cups mounted proximate opposite ends thereof, the headband being dimensioned to apply a resilient biasing force to the collector cups to bias the C-shaped ridge into contact with the user's head proximate the user's ears to transmit collected sound vibrations through the C-shaped ridge to the user's bone structure proximate the ears and resist the entry of sounds other than from in front of the user from entering the collector cups.

BRIEF DESCRIPTION OF THE DRAWINGS

FIG. 1 is a perspective view of a non-electronic acoustic hearing aid made in accordance with the present invention.

FIG. 2 is a front elevation view of the present hearing aid, with a user's head shown in phantom.

FIG. 3 is a top plan view of the present hearing aid, with a user's head shown in phantom.

FIG. 4 is a sectional side elevation view of the present hearing aid taken along line 4—4 in FIG. 5, with a user's ear shown in phantom.

FIG. 5 is a sectional side elevation view of the present hearing aid taken along line 5—5 in FIG. 1.

FIG. 6 is a sectional bottom plan view of the present hearing aid taken along line 6—6 in FIG. 5.

BEST MODE FOR CARRYING OUT THE INVENTION

Non-electric acoustical hearing aids are well known. These devices tend to be classifiable into a first family consisting of a large cup or scoop for capturing and focusing sound waves into a user's ear canal, or a second family which consists of a small tube inserted into the ear, typically accompanied by a small external member covering this tube thereby enclosing a small cavity of air adjacent to the ear. Each of these different families of acoustic hearing aids suffer from numerous disadvantages which are overcome by the present invention, as will be set out herein.

As seen in the accompanying FIGURES, a non-electronic acoustic hearing aid 10 is provided. Hearing aid 10 is composed of a pair of thick-walled sound collector cups 12 and an arcuate headband 14. Collector cups 12 are each shaped to fit substantially over and around the pinna of a user's ears, contacting the back 21 of the pinna and turning the back of the pinna forward, as is best seen in FIGS. 2 and 4.

Cups 12 are made of a sound reflective material, which will be set forth in more detail herein, and act as acoustic sound collectors which serve to collect and focus the sound waves emanating from sources directly in front of the user. These sound waves which emanate from sources directly in front of the user will strike inner surface 18 and then be reflected into the user's ear canals. The basic principle of using scoops or collectors for collecting and focussing sound waves into a user's ear canals, and thereby magnifying their amplitude as heard by the user, is well known. However, collector cups 12 of the present invention have a novel structure and provide numerous advantages not seen in the prior art, as will be set forth.

The present collector cups 12 are much thicker than existing designs of collector cups. Typically, cups 12 are shaped to have a thickness varying between at least ¼ to ½ inch at various locations. Being formed from a sufficiently thick block of sound reflective material, cups 12 are therefore able to effectively reflect sound waves from all of their surfaces and are thus also able to minimize the transmission of sound waves therethrough. This reflective property enables cups 12 to reflect and focus sound waves into the user's ear canals 22 when such sound waves strike inner surface 18, yet also provides acoustic insulation against sound transmission through cups 12 from sound waves hitting outer surface 19 of cups 12. Accordingly, sound waves hitting outer surface 19 of cups 12 will be reflected away from the user's ears at the same time that sound waves hitting inner surface 18 of cups 12 will be reflected into the user's ear canals 22. The turning of the back 21 of the user's ear pinna 20 forward further helps to amplify and focus sound waves into the user's ear canals 22.

Consequently, the acoustically reflective properties of cups 12 provide a directional selectivity to the present invention. Specifically, only the sound waves directly striking inner surface 18 will be the sound waves focussed into ear canals 22. These sound waves directly hitting inner surface 18 will only be those emitted from sources directly in front of the user. Accordingly, by orienting their head to point to any particular direction, a user effectively amplifies the sounds coming from that direction, and dramatically reduces background sounds coming from other directions, thus providing both amplification and clarity for the user.

For many people with hearing problems, distinguishing between various sounds is as much a problem as detecting the presence of these sounds. With the present hearing aid's directional selectivity, (amplifying sounds emitted in front of the user and reflecting away sounds emitted from other directions), a user is easily able to both select a particular sound source, and listen to this sound source at an amplified volume, with background noise being dramatically reduced. This feature is particularly desirable when the user wishes to listen to sounds emitted from a person sitting across from them, a television set, a stereo system or a movie screen. Accordingly, the present invention provides a system assisting both those persons having trouble actually hearing sounds and those persons hearing sounds but having trouble distinguishing between various sounds.

Collector cups 12 have a C-shaped ridge 17 which is formed for direct engagement with the sides of the user's head immediately proximate and substantially around the user's pinna. As is best seen in FIG. 4, ridge 17 extends from a position in front of the top of pinna 20, above the level of ear canal 22 around pinna 20 to a position below earlobe 23.

Collector cups 12 further extend outwardly from ridge 17 and away from the user's head and extend forwardly in a generally parallel relation to the user's head to a position in advance of the user's ear canal 23. The unique shape of collectors 12, having their inner surface 18 generally parallel to the sides of the user's head, extending in front of ear canals 23, enables cups 12 to reduce sound reception from sources emitted at the sides of the user's head.

Cups 12 terminate in a forwardly facing, substantially vertically oriented, generally rectangular opening 25 for receipt and collection of sounds emanating in front of the user. Opening 25 is much narrower than was typical of existing acoustic hearing aids which instead had large cup or scoop shaped sound reflectors protruding outwards from the user's ears. Experimentation has shown that for best results, opening 25 typically has a height to width ratio of at least 3 to 1, but a height to width ration of at least 2 to 1 is also acceptable.

An advantage, therefore, of the present invention is its aesthetic appeal over existing large, wide and bulky sound scoops. Moreover, not being as wide as existing sound scoops, the present invention can be constructed to be lightweight. The present invention, therefore, avoids the large, wide and consequently non-aesthetically appealing sound scoops found in the first family of pre-existing designs without having to resort to the very invasive, narrow frequency of operation designs of the second family of hearing aids. Instead, the present invention's novel shape for cups 12 and inner surface 18 in particular, has been shown by experimentation to achieve sound amplification in the present invention on the order of 25 dB in the frequency range of 1,500 kHz, (which is a common frequency for human speech, and therefore one much desired to be amplified). Important advantages of the present invention are that it gathers and amplifies sound waves over a wide range of frequencies, without requiring any form of frequency "tuning" for different users. This property was not seen in the second above-discussed family of acoustic hearing aids.

As is seen in FIG. 4, ridge 17 has a large stub 26 at its top end which is positioned slightly forward of the user's ear to hook over the front of the user's ear when wearing the hearing aid. Furthermore, ridge 17 has a downwardly sloping front lip 24 positioned at its bottom end. The presence of the stub 24 and sloping front lip 26 has been determined by experimentation to enhance the acoustic performance of the present hearing aid.

An arcuate headband 14 is provided to support cups 12 against the user's head. Headband 14 is preferably formed of a resiliently flexible material. This material preferably would be the same material used in forming cups 12 as set out above. Headband 14 is dimensioned to apply a resilient biasing force to cups 12 such that ridge 17 is biased into contact with the user's head proximate the user's ears. This biasing contact between ridge 17 and the user's head enables collected sound vibrations to be transmitted through ridge 17 to the bone structure proximate the ears, thereby assisting in amplifying sounds entering cups 12 from sound sources in front of the user, while sealing cups 12 around the back of the user's ears, thus resisting the entry of sounds emitted from directions other than those directly in front of the user's ears. Biasing force in headband 14 is preferably maintained by the passage of a deformable wire 30 which can be imbedded in headband 14 during its molding. Moreover, wire 30 adds stiffness to the headband, allowing headband 14 to be deformed slightly in shape so as to fit tightly, yet comfortably on the heads of each particular user, thus fitting a range of different user head sizes.

Cups 12 are held to arcuate headband 14 at joints 16, which allow for some limited motion enabling the user to best position receptacles 12 to properly contact the sides of their head. As is best seen in FIG. 5, joints 16 are preferably composed of a stud 32 through which both wire 30 and a wire 34 pass, thus anchoring cups 12 to headband 14.

The acoustically reflective material from which cups 12 are preferably made of plastics such as Polyol 1 (containing tertiary amine) produced by Urethane Technology Inc. of Orange County California. This material has excellent sound reflective properties and been shown to be particularly well suited to accomplishing all the above listed objectives of the present invention. Specifically, this material reflects a full range of the spectrum of sound waves into the ear canal of the user, without significant discrimination between various ranges in the sound frequency spectrum. Therefore, the present invention has the advantage of operating well over a large range of frequencies, something which could not be achieved by many prior art designs. This plastic material is lightweight, inexpensive and can easily be injection molded to form the novel contoured shape of cups 12, thus keeping manufacturing costs low. Another advantage of using this material is that the same material can be used to injection mold headband 14, thus potentially yielding additional cost savings.

As can be seen, there are few parts in the present invention. Moreover, the present invention comprises no parts which move during its operation. No electrical components are required to fabricate the present invention. Accordingly, the present design is very simple and durable, in addition to being very inexpensive and easy to manufacture and has no repair or operating costs. As can also be seen, the present invention does not require any invasive tubular members be inserted into the user's ear canals, providing further advantages over the second family of prior art designs.

What is claimed is:

1. An acoustic hearing aid comprising:

a) a pair of thick-walled, sound collector cups each shaped to fit over the pinna of a user's ear, in a manner that contacts the back of the pinna and turns the back of the pinna forward, and each constructed of a sound reflective material of sufficient thickness to provide insulation against sound transmission therethrough from a side of said collector cups, said collector cups each having a C-shaped ridge of substantial thickness dimension formed for engagement of the user's head immediately proximate and around the user's pinna, said ridge extending from a position in front of the top of the pinna and above the level of the ear canal around the pinna to a position below the earlobe, said collector cups each further extending outwardly from said ridge and away from the user's head and extending forwardly in a generally parallel relation to the user's head to a position in advance of the ear canal to reduce sound transmission to the user's ears from the sides of the user's head, said collector cups each terminating in a forwardly facing, substantially vertically oriented, generally rectangular opening for receipt and collection of sound emanating from the front of the user; and b) an arcuate headband constructed of a resiliently flexible material and having said collector cups mounted proximate opposite ends thereof, said headband being dimensioned to apply a resilient biasing force to said collector cups to bias said C-shaped ridge into contact with the user's head proximate the user's ears to transmit collected sound vibrations through said C-shaped ridge to the user's bone structure proximate the ears and resist the entry of sounds other than from in front of the user from entering said collector cups.

2. The acoustic hearing aid as defined in claim 1 wherein, said collector cups are formed of plastic.

3. The acoustic hearing aid as defined in claim 1 wherein, said collector cups have a wall thickness of at least about ¼ to ½ inches.

4. The acoustic hearing aid as defined in claim 3 wherein, said opening has a height to width ratio of at least about 2 to 1.

5. The acoustic hearing aid as defined in claim 4 wherein, said opening has a height to width ratio of at least about 3 to 1.

6. The acoustic hearing aid as defined in claim 1 wherein, said collector cups each have a downwardly sloping front lip proximate the user's earlobe.

7. The acoustic hearing aid as defined in claim 1 wherein, said collector cups each have a large stub at their top ends that are positioned slightly forward of the user's ear.

8. The acoustic hearing aid as defined in claim 7 wherein, said collector cups each have a downwardly sloping front lip proximate the user's ear lobe.

* * * * *